(12) United States Patent
Turner (10) Patent No.: US 11,123,470 B2
(45) Date of Patent: Sep. 21, 2021

(54) CONTROL SYSTEM

(71) Applicant: Spectrum Medical Ltd., Gloucester (GB)

(72) Inventor: Stephen Turner, Gloucester (GB)

(73) Assignee: Spectrum Medical Ltd., Gloucester (GB)

( * ) Notice: Subject to any disclaimer, the term of this patent is extended or adjusted under 35 U.S.C. 154(b) by 491 days.

(21) Appl. No.: 15/745,896

(22) PCT Filed: Jul. 21, 2016

(86) PCT No.: PCT/GB2016/052212
§ 371 (c)(1),
(2) Date: Jan. 18, 2018

(87) PCT Pub. No.: WO2017/013435
PCT Pub. Date: Jan. 26, 2017

(65) Prior Publication Data
US 2018/0207348 A1    Jul. 26, 2018

(30) Foreign Application Priority Data
Jul. 21, 2015    (GB) ...................................... 1512840

(51) Int. Cl.
*A61M 1/36*    (2006.01)
*A61M 1/14*    (2006.01)
(Continued)

(52) U.S. Cl.
CPC ............ *A61M 1/3664* (2013.01); *A61M 1/14* (2013.01); *A61M 1/3627* (2013.01);
(Continued)

(58) Field of Classification Search
CPC .... A61M 1/3664; A61M 39/281; A61M 1/14; A61M 1/101; A61M 1/3666;
(Continued)

(56) References Cited

U.S. PATENT DOCUMENTS 5,584,806 A    12/1996    Amano
5,702,358 A    12/1997    Witherspoon et al.
(Continued)

FOREIGN PATENT DOCUMENTS

EP    1 464 349       10/2004
WO    WO 96/25972     8/1996
(Continued)

OTHER PUBLICATIONS

United Kingdom Intellectual Property Office, Search Report under Section 17(5)—Application No. GB1512840.8, dated Jan. 11, 2016, 3 pages.
(Continued)

*Primary Examiner* — Tatyana Zalukaeva
*Assistant Examiner* — Jessica R Arble
(74) *Attorney, Agent, or Firm* — Sunstein LLP (57) ABSTRACT

A cardioplegic agent delivery system comprises a supply reservoir (40) for a cardioplegic agent carrier fluid, a delivery channel from the supply reservoir (40) to an outlet (48), and a pump (50) to flow the carrier liquid in the delivery channel above a minimum driving pressure. The supply reservoir (40) is configured to hold carrier fluid below the minimum driving pressure. The pump (50) is a centrifugal pump configured to receive carrier fluid from the supply reservoir (40) and to flow the carrier fluid to the outlet (48) at a flow rate and above the minimum driving pressure for the delivery of cardioplegic agent. This allows cardioplegia delivery to be managed better.

19 Claims, 3 Drawing Sheets

(51) Int. Cl.
*A61M 60/205* (2021.01)
*A61M 39/28* (2006.01)
(52) U.S. Cl.
CPC ........ *A61M 1/3666* (2013.01); *A61M 39/281* (2013.01); *A61M 60/205* (2021.01); *A61M 2205/3334* (2013.01); *A61M 2205/3355* (2013.01); *A61M 2205/3386* (2013.01); *A61M 2205/3389* (2013.01)
(58) Field of Classification Search
CPC ........ A61M 1/3627; A61M 2205/3386; A61M 2205/3389; A61M 2205/3355; A61M 2205/3334
See application file for complete search history.

(56) References Cited

U.S. PATENT DOCUMENTS

| | | | | |
|---|---|---|---|---|
| 5,957,137 | A | * | 9/1999 | Dalke ................ G05D 11/132 128/898 |
| 5,957,879 | A | | 9/1999 | Roberts et al. |
| 6,632,189 | B1 | | 10/2003 | Fallen et al. |
| 2001/0010802 | A1 | * | 8/2001 | Tamari ................ A61M 1/3667 422/41 |
| 2003/0163078 | A1 | * | 8/2003 | Fallen ................ A61M 1/3666 604/6.01 |
| 2005/0084416 | A1 | * | 4/2005 | Thomas ................ A61M 1/32 422/45 |
| 2005/0085762 | A1 | | 4/2005 | Vijay et al. |
| 2011/0257579 | A1 | * | 10/2011 | Rossi ................ A61M 1/36 604/6.15 |

FOREIGN PATENT DOCUMENTS

| | | |
|---|---|---|
| WO | WO 2005/039687 | 5/2005 |
| WO | WO 2012/141756 | 10/2012 |

OTHER PUBLICATIONS

Malte Kaden, Authorized officer European Patent Office, International Search Report—Application No. PCT/GB2016/052212, dated Sep. 29, 2016, together with the Written Opinion of the International Searching Authority, 11 pages.
European Patent Office, Office Action dated May 15, 2020 for European Application No. 16744479.3 (5 pages).

* cited by examiner

CONTROL SYSTEM

FIELD OF THE INVENTION

The present invention relates to a system and method for cardioplegia management, in particular for use in cardioplegia management during surgery. More specifically, the present invention relates to a system for preparing a cardioplegic solution for delivery under safe conditions, so that the cardioplegic solution may subsequently be administered to a patient at conditions set by the system.

BACKGROUND

During surgery on the heart, such as cardiac bypass surgery, surgeons stop the heart to enable them to operate on a still heart. The heart can be stopped by administering a cardioplegic solution, which is a solution containing agents capable of suppressing heart muscle activity. While the heart is stopped, a heart-lung machine (HLM) is used to maintain a supply of oxygenated blood to the patient to keep the patient alive during surgery. A HLM comprises a perfusion circuit in which venous blood is drawn from a patient, oxygenated, and administered arterially to a patient. For the administration of cardioplegic solution, it is conventional to draw a portion of blood from the (principal) arterial perfusion line of the HLM into a (secondary) cardioplegia line and to use the blood as a carrier fluid to be infused with cardioplegic agent. Once infused with cardioplegic solution, the carrier fluid may be administered as a cardioplegic solution towards the heart.

The concentration of the cardioplegic solution must be carefully controlled within narrow margins. If the concentration of the cardioplegic solution is too low, the suppressive effect may cease early and a heart may unexpectedly beat during surgery. Too high a concentration of the cardioplegic solution can be damaging to the heart or patient.

It is therefore important that a cardioplegic solution is delivered to a patient at an appropriate pressure, flow rate and concentration, and in appropriate intervals.

For instance, WO 2005/039687 A1 discloses an oxygenation controller in which oxygenation control and cardioplegia delivery are integrated. The oxygenation controller mixes an oxygenated blood input and a deoxygenated (venous) blood input into a reservoir to hold a mixture of deoxygenated blood and oxygenated blood, thereby providing a mixed blood supply. The flow of oxygenated blood toward the reservoir is controlled by a first pump (for oxygenated blood). The flow of deoxygenated blood toward the reservoir is controlled by a second pump (for deoxygenated blood). The flow of mixed blood is controlled by a third pump (for mixed blood), which pumps the mixed blood to a cardioplegia solution injector. The pressures and flow rates effected by the first pump and the second pump risk a 'pushing-through' of blood through the reservoir. A pushing-through causes uncontrolled flow to the cardioplegia solution injector. Thus, in order to be able to provide cardioplegia delivery at a flow rate and at a driving pressure for the delivery of cardioplegic agent, the third pump (for mixed blood) of WO 2005/039687 A1 must be able to block the flow of blood, i.e., the third pump must be a so-called "occlusive" pump.

The present invention seeks to provide an improved cardioplegic agent delivery system.

SUMMARY OF THE INVENTION

In accordance with a first aspect of the present invention, there is provided a cardioplegic agent delivery system as defined in claim 1.

The cardioplegic agent delivery system comprises a supply reservoir for a carrier fluid for the cardioplegic agent, a delivery channel for the carrier fluid, wherein the delivery channel leads from the supply reservoir to an outlet of the delivery channel, a pump configured to effect a flow of the carrier liquid in the delivery channel from the supply reservoir to the outlet above a minimum driving pressure for the delivery of cardioplegic agent. The supply reservoir is configured to hold carrier fluid below the minimum driving pressure, and the pump is a centrifugal pump configured to receive carrier fluid from the supply reservoir and to effect a flow of the carrier fluid to the outlet at a flow rate and above the minimum driving pressure for the delivery of cardioplegic agent.

Cardioplegic solutions need to be administered to a patient at an appropriate driving pressure within narrow margins. Over-pressurising is a problem because it increases the strain on the components of the delivery system. Over-pressurising may also be hazardous to a patient, for instance, by causing damage to heart tissues. This is especially an issue with delivery of cardioplegic solution to the coronary sinus (a typical target site for cardioplegic agent). An under-pressurised cardioplegic solution is not in a condition for subsequent administration to a patient, because of the risk of back flow due to the pressure of other fluids in the system.

The expressions "back flow" and "retrograde flow" may be used interchangeably in day-to-day language, and even in the surgical field.

By "back flow", it is meant that a fluid flows in a direction opposite of the intended direction. E.g., in a channel intended for delivery of a fluid from a supply reservoir toward a pump, the fluid would flow toward the supply reservoir in the event of back flow.

By "retrograde" flow, it is meant that a fluid is purposefully channelled to flow in a direction other than a conventional direction.

Put briefly, back flow is undesired, whereas retrograde flow is purposive. In a retrograde flow channel in which it is intended to deliver a fluid toward a patient (e.g., from a pump), back flow means that the fluid flows from the patient (e.g., toward the pump). Back flow may prevent a volume of cardioplegic solution from reaching the desired organ and render dosing unreliable.

By "minimum driving pressure", it is meant that the pressure is sufficiently high to avoid back flow.

Cardioplegic agent is normally administered via a carrier fluid, such as blood or saline solution. To control the flow rate of the cardioplegic agent carrier fluid, it is conventional to use peristaltic pumps (also called roller pumps) or actuator pumps, such as a piston pump or a membrane pump.

There is, however, a problem with conventionally used pumps. In the event of excess pressure, i.e. when pressure levels are exceeded at which a cardioplegic delivery system may be operated safely, peristaltic pumps or actuator-driven pumps may lack responsiveness to quickly enough stop pumping in an automated emergency shut-down. In the short period between a pressure-build up and the emergency shut-down, a peristaltic pump may continue to increase the pressure further, leading to the disruption of tubing or connections and the ensuing distribution of carrier fluid (e.g., blood) in the operating environment.

To appreciate the problem, it must be borne in mind that—despite best practice—inadvertent clamping or pinching of high pressure lines of a perfusion system can occur during surgery. This is because in a surgical environment there are a large number of personnel operating in a small space containing a large amount of tubing. Inadvertent clamping or pinching may result in a peak pressure, or pressure spike, in the cardioplegia line, requiring an emergency shut-down of a cardioplegia pump.

Another problematic property of peristaltic pumps is that they are relatively robust at pumping air bubbles. If, for any reason, air bubbles enter the cardioplegia line, a peristaltic pump will be able to relay the air bubbles towards the patient, risking air embolism (an air bubble blocking a blood vessel). This poses a safety hazard.

A solution to these problems can be provided by centrifugal pumps. Centrifugal pumps are inherently pressure-limited, and are therefore less prone to further exacerbate a pressure build-up in the event of an inadvertently caused pressure spike. Also, centrifugal pumps lose efficiency when air is entrained in them, because this causes a centrifugal pump to de-prime. While a loss of efficiency through de-priming is still a matter requiring attention, it is of a lesser concern with regard to patient safety, because a centrifugal pump is less likely to pump air toward a patient.

However, centrifugal pumps were hitherto not used to pump cardioplegic carrier fluid to a patient, because it is conventional to use a supply of pressurised carrier fluid from a high-pressure arterial line of an oxygenator, to avoid back flow. Centrifugal pumps are inherently unable to modulate the flow rate of highly pressurised carrier fluid to the correct pressure for cardioplegia delivery.

To provide further detail, conventionally, the carrier fluid is pressurised to a pressure higher than coronary pressures where the cardioplegic agent is delivered. This may be a pressure suitable for driving the carrier fluid. The pressurising of the carrier fluid may be achieved, e.g., by positioning the supply reservoir higher than a patient, or by using blood withdrawn from an arterial line of an oxygenator, because arterial blood leaves an oxygenator in a highly pressurised condition. To illustrate the magnitudes involved with examples, the pressure in an arterial line of a perfusion system may routinely be at 200 to 300 mmHg (26.7 to 40.0 kPa), as opposed to the mean coronary pressures in the region of 20 to 120 mmHg (2.67 to 16.0 kPa). The driving pressure of a cardioplegia line may be as little as 20 mmHg and may, intermittently, reach levels in the region of 300 mmHg. As such, the minimum driving pressure of a cardioplegia pump may be as low as about 20 mmHg. It is understood that, in the field, pressures are conventionally provided in mmHg relative to atmospheric pressure (1 atm corresponds to 101.325 kPa, or 760 mmHg). A blood pressure of 100 mmHg (above atmospheric pressure) would correspond to a total pressure of 860 mmHg.

It will be understood that the driving pressure, i.e., the pressure required to deliver a fluid towards a patient, may depend on various factors, including the posture of a patient and the body location at which the cardioplegic solution is to be administered. However, arterial blood leaving the oxygenator at a pressure of about 200 to 300 mmHg can be assumed to always have a minimum driving pressure, in order to achieve the desired blood flow rates towards (and into) a patient.

Conventional pumps are occlusive pumps. An occlusive pump is understood to be a pump that may block the flow of fluid through the pump. E.g., a peristaltic pump comprises a roller arrangement on a rotor to compress one or more portions of flexible tube containing fluid. By rotating the roller arrangement, the portions at which the tube is compressed may be moved along the tube, forcing a volume of fluid through the tube. A compressed portion constitutes an occlusion. Another example of an occlusive pump is an actuator-driven pump, such as a piston pump or a membrane pump, which, when operated appropriately, can block the flow of pressurised liquid through the pump.

Occlusive pumps isolate to a degree the pressure upstream of the pump from the pressure downstream of the pump. As such, the pressure and flow rate downstream of an occlusive pump can be regulated regardless of the line pressure upstream of the pump. Particularly for driving the flow of a cardioplegic agent carrier fluid, where avoiding unregulated peak pressures is a predominant concern, occlusive pumps are thus believed to be without alternative.

This is because, if a non-occlusive pump were used, such as a centrifugal pump, the pressurised carrier fluid would push through the pump, and render it practically impossible to control the pressure levels downstream of the pump.

Against conventional practice, the present applicant has appreciated that the use of a centrifugal pump in a cardioplegia line can be enabled by ensuring that carrier fluid at a pressure below the minimum driving pressure is used to supply the centrifugal pump.

The combination of a carrier fluid supply at less than driving pressure and a centrifugal pump offers an advantage. In addition to avoiding the aforementioned problems that exist with peristaltic pumps, centrifugal pumps are more responsive to effect changes in flow rates and pressure that may be required due to changes in vessel tone (physiological blood vessel constriction or dilation). The responsiveness of centrifugal pumps further increases dosing accuracy.

In some embodiments, the cardioplegic agent delivery system further comprises a back-flow prevention device downstream of the supply reservoir, to prevent flow from the delivery channel downstream of the supply reservoir into the supply reservoir.

The risk of under-pressurisation may remain a concern when using a centrifugal pump in a cardioplegia line, because the centrifugal pump may only be operated infrequently. The risk can be mitigated by providing a back-flow prevention device in the delivery channel. The back-flow prevention device prevents back flow from an area of higher pressure to an area of lower pressure, e.g. back flow toward the supply reservoir.

In some embodiments, the cardioplegic agent delivery system further comprises a back-flow prevention device downstream of the centrifugal pump, to prevent flow from the delivery channel downstream of the centrifugal pump into the centrifugal pump.

The back-flow prevention device may be positioned downstream of the centrifugal pump, to prevent back flow toward the centrifugal pump.

In some embodiments, the back-flow prevention device comprises a back-flow prevention valve and/or an automated clamping system.

The back-flow prevention device may be provided in the form of a non-return valve, such as a one-way duck bill valve, or a clamp or a clamping system. The back-flow prevention device may be automated.

In some embodiments, the supply reservoir is a venous reservoir of a perfusion system.

If a cardioplegic agent delivery system is operated in conjunction with a perfusion system, the perfusion system will comprise a venous reservoir from where blood is to be drawn towards an oxygenator. One property of centrifugal pumps is that they need to be operated in a primed condition. This means that the centrifugal pump needs to be filled with fluid to operate. Operating an unfilled centrifugal pump can negatively affect the pump performance. As perfusion systems are typically configured to maintain a minimum volume of blood in the venous reservoir, the blood in the venous reservoir is a reliable source of carrier fluid. This helps ensuring that there is sufficient fluid to prevent the centrifugal pump from de-priming.

Furthermore, in order to ensure that the venous blood drains into the venous reservoir, the venous reservoir is typically located below a patient, or operated under vacuum-assisted venous drainage, to encourage drainage away from the patient and toward the venous reservoir. Thus, in any circumstances, the pressure of the venous blood in the venous reservoir can be assumed have less than a minimum driving pressure. This makes the venous reservoir a convenient source of such a carrier fluid.

In some embodiments, the supply reservoir is provided downstream of an oxygenator of a perfusion system, and the delivery system further comprises a pressure-isolating device between the oxygenator and the supply reservoir, to provide that the pressure of the carrier fluid in the supply reservoir is below the minimum driving pressure independently of the pressure of the carrier fluid upstream of the pressure-isolating device.

This allows arterial, i.e., oxygenated, blood to be used as a carrier fluid for the cardioplegic agent. However, arterial blood leaves the oxygenator at a high pressure, suitably high to drive the fluid, as set out above. A pressure-isolating device allows the pressure of the carrier fluid to be reduced. For instance, the pressure-isolating device may temporarily cut off the flow of carrier fluid into supply reservoir. When cut off, blood from the arterial line past the cut-off may continue to flow into the supply reservoir, but in the supply reservoir, the blood is no longer pressurised. The supply reservoir is configured to hold the carrier fluid, in this case, arterial blood, below a minimum driving pressure, suitable for use with a centrifugal pump.

The pressure-isolating device may be provided in the form of a clamp. The clamp may be released intermittently to permit flow of arterial blood into the supply reservoir for refilling. In this regard, the amount of carrier fluid required in the supply reservoir, for cardioplegia delivery, is normally small, because the flow rate of cardioplegic solution is in the region of millilitres per minute (typically 10 ml/min, average of 200-300 ml/min, sometimes as high as 500 ml/min), as opposed to the standard arterial flow rates of 4-6 litres per minute.

In some embodiments, the system is further configured to receive an input indicative of the amount of carrier fluid in the supply reservoir, to make a determination as to whether or not the amount of carrier fluid is below a threshold level, and to actuate the pressure-isolating device to permit flow of carrier fluid into the supply reservoir.

The pressure-isolating device may be in the form of an automated clamping system. I.e., the pressure-isolating device will also constitute a flow-isolating structure. A controller may be programmed to operate the automated clamping system in response to a fluid level in the supply reservoir. If the fluid level in the supply reservoir indicates that the amount of carrier fluid is below a minimum threshold, the automated clamping system may operate to permit flow of carrier fluid into the inlet of the supply reservoir, to increase the amount of carrier fluid therein. If the fluid level in the supply reservoir indicates that the amount of carrier fluid is above a maximum threshold, the automated clamping system may operate to stop flow of carrier fluid into the inlet of the supply reservoir, to arrest an increase of carrier fluid in the supply reservoir.

In some embodiments, the outlet of the delivery channel supplies a cardioplegic line.

As the cardioplegic agent delivery system comprises a pump that renders the carrier fluid in a condition (pressure and flow rate) suitable for the administration of cardioplegic agent, the outlet may conveniently be connected to a cardioplegic line.

In some embodiments, the cardioplegic agent delivery system further comprises a cardioplegic agent inlet downstream of the pump.

This allows the cardioplegic agent to be administered into the carrier fluid after the flow rate and pressure of the carrier fluid has been set by the centrifugal pump. This helps to ensure that cardioplegic agent is only administered when the carrier fluid is flowing at pre-defined conditions, e.g., at a minimum flow rate or above a minimum driving pressure. This improves dosing accuracy by reducing the risk of a stagnant volume of cardioplegic solution, because a more precise assumption can be made about when an amount of cardioplegic agent administered into the carrier fluid will subsequently reach the desired organ.

In some embodiments, the cardioplegic agent delivery system further comprises a level sensor configured to monitor the amount of fluid in the supply reservoir.

This allows a determination to be made of the amount of carrier fluid in the supply reservoir. If the amount of carrier fluid in the reservoir is below a level that is safe to operate a centrifugal pump, a mitigating action may be initiated. For instance, a signal may be generated to alert an operator of the amount of fluid.

In embodiments configured to actuate a pressure-isolating device in response to an input indicative of the amount of carrier fluid in the supply reservoir, the input may be provided by the level sensor. In such embodiments, the mitigating action may be to permit carrier fluid to flow into the supply reservoir.

In some embodiments, the supply reservoir is or comprises a collapsible container.

A collapsible container, such as a bag made from soft material, is able to collapse or expand depending on the amount of carrier fluid inside, but within a volume limit. This property renders collapsible containers inherently safer than open reservoirs, because there is no possibility of blood overflowing and less risk of contamination, and less risk of entraining air.

In some embodiments, the cardioplegic agent delivery system further comprises a flow sensor for sensing the flow of the carrier fluid downstream of the centrifugal pump.

In some embodiments, the cardioplegic agent delivery system further comprises a pressure sensor for sensing the pressure of the carrier fluid downstream of the centrifugal pump.

This allows the flow rate to be determined and a feedback to be provided. For instance, the centrifugal pump may be controlled to flow the carrier fluid at a pre-defined flow rate and/or pressure, or to ensure a minimum flow rate and/or pressure, or to remain below a maximum flow rate and/or pressure of the carrier fluid downstream of the centrifugal pump.

A control of the centrifugal pump in response to the flow sensed by a flow sensor may constitute a feedback loop, or closed loop control, permitting the flow rate to be kept at a pre-defined level. Likewise, a control of the centrifugal pump in response to the pressure sensed by a pressure sensor may constitute a feedback loop, or closed loop control, permitting the pressure to be kept at a pre-defined level.

As mentioned above, a typical flow rate of a cardioplegia carrier fluid is in the region of typically 200-300 ml/min, which is an order of magnitude below the standard arterial flow rates of 4-6 litres per minute. Controlling the flow rate of the carrier fluid and/or the pressure of the carrier fluid allows the appropriate flow rates and/or pressure levels to be controlled independently of the standard arterial flow rates.

The flow sensor may be coupled with the back-flow prevention device. If the flow rate is indicative of a risk of back flow, the back-flow prevention device may be actuated to prevent or stop back flow.

In some embodiments, the cardioplegic agent delivery system further comprises a controller for controlling the centrifugal pump, the back-flow prevention device, and/or the pressure-isolating device in response to a control signal.

This facilitates an automated operation of the components of the cardioplegic agent delivery system.

In some embodiments, the controller comprises a processor and software instructions implemented by the processor.

The software instructions are effective to control the centrifugal pump, the back-flow prevention device, and/or the pressure-isolating device, for instance in response to a control signal.

DESCRIPTION OF THE FIGURES

Exemplary embodiments of the invention will now be described with reference to the Figures, in which.

DESCRIPTION

Figure 1:
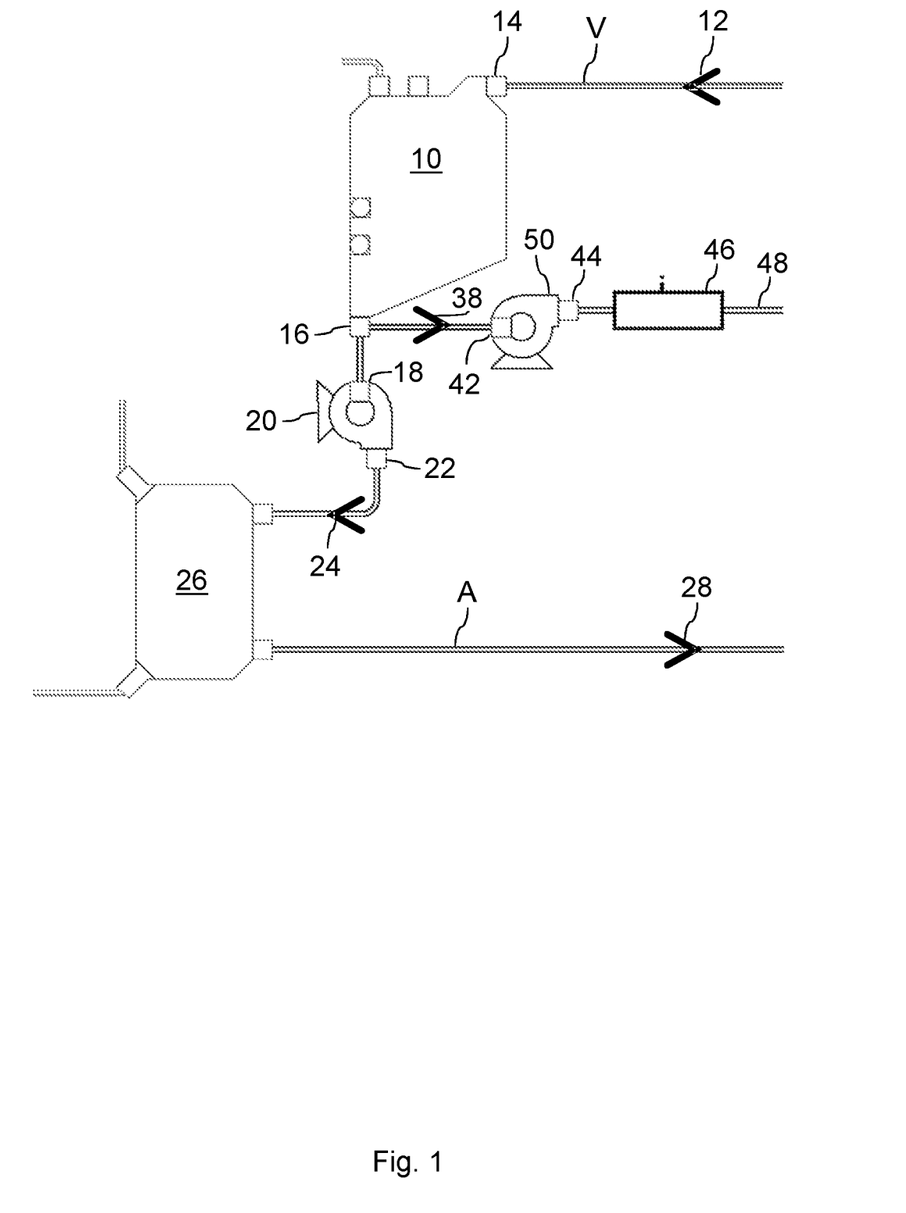
FIG. 1 shows a schematic arrangement of an exemplary embodiment of a cardioplegic agent delivery system.

FIG. 1 shows an embodiment of a cardioplegic agent delivery system installed as part of a perfusion system. Extracorporeal perfusion is a process in which blood from a patient is circulated outside the patient's body and re-oxygenated to be returned to the patient. More specifically, venous (oxygen-reduced) blood which has been removed from a patient via a venous line is oxygenated by exposure to an oxygenation gas in an oxygenator for supply via an arterial line back to the patient as arterial blood.

Core components of the perfusion system are a blood reservoir 10 and an oxygenator 26. A venous line V is provided upstream of the blood reservoir 10 to receive venous (oxygen-reduced) blood received from, for instance, a patient. In the venous line V, blood flows in a direction indicated by arrow 12 into the blood reservoir 10 via a reservoir inlet 14. The blood reservoir 10 is also called a "venous reservoir".

The blood reservoir 10 comprises a reservoir outlet 16 from which blood may be drawn by activation of a pump 20 located downstream of the blood reservoir 10 in a direction indicated by arrow 24. The blood is pumped via a pump inlet 18 through the pump outlet 22 and towards the oxygenator 26 in which the blood is supplied with oxygenation gas to re-oxygenate the blood as arterial blood. The re-oxygenated, or arterial, blood leaves the oxygenator 26 at high pressure via an arterial line A in the direction of arrow 28 and may then be supplied, for instance, to a patient. By high pressure, it is meant that the pressure is so high that the blood would push through a non-occlusive pump.

Conventionally, administration of cardioplegic solution is achieved by diverting a secondary flow path from the arterial line. A volume of cardioplegic solution may be injected into the arterial blood in the secondary flow path, to be administered to a patient.

In FIG. 1, the secondary flow path is branched off from the reservoir outlet 16, directly downstream of the venous reservoir and configured to draw blood from the reservoir outlet 16. Alternatively, the secondary flow path may be connected directly to the blood reservoir 10, to originate from there. As shown in FIG. 1, the reservoir outlet 16 is upstream of the pump inlet 18 of the pump 20 and so it is understood that fluid in the secondary flow path is not pressurised by pump 20. The blood reservoir 10, constituting a supply reservoir, is configured to hold carrier fluid, constituted by venous blood, in a non-pressurised condition, i.e., below a minimum driving pressure. The blood may be below a minimum driving pressure by virtue of being positioned lower than the patient. The blood may be below a minimum driving pressure because the blood reservoir 10 employs vacuum-assisted venous drainage to draw blood from a patient.

The secondary flow path allows blood to be pumped in the direction indicated by arrow 38 towards a pump inlet 42 of a centrifugal pump 50, through the pump outlet 44. Blood exiting the pump outlet 44 has a flow rate determined by the centrifugal pump 50. Downstream of the centrifugal pump 50, a cardioplegic agent delivery module 46 is provided, configured for administering cardioplegic agent into the blood stream. At a location 48 in the secondary flow path, downstream of the centrifugal pump 50 and the cardioplegic agent delivery module 46, the blood is in a condition for subsequent administration to a patient, i.e., the blood has the appropriate flow rate and driving pressure, and has the appropriate concentration of cardioplegic agent. To provide illustrative values in line with what was mentioned above, the arterial flow rate in the arterial line A in direction of arrow 28 is typically in the region of 4-6 litres per minute, whereas the flow rate of the carrier fluid at location 48 is typically in the region of 200-300 ml per minute. It will be understood that the flow rate determined by the centrifugal pump 50 is thus controlled independently of the arterial flow rate.

Figure 2:
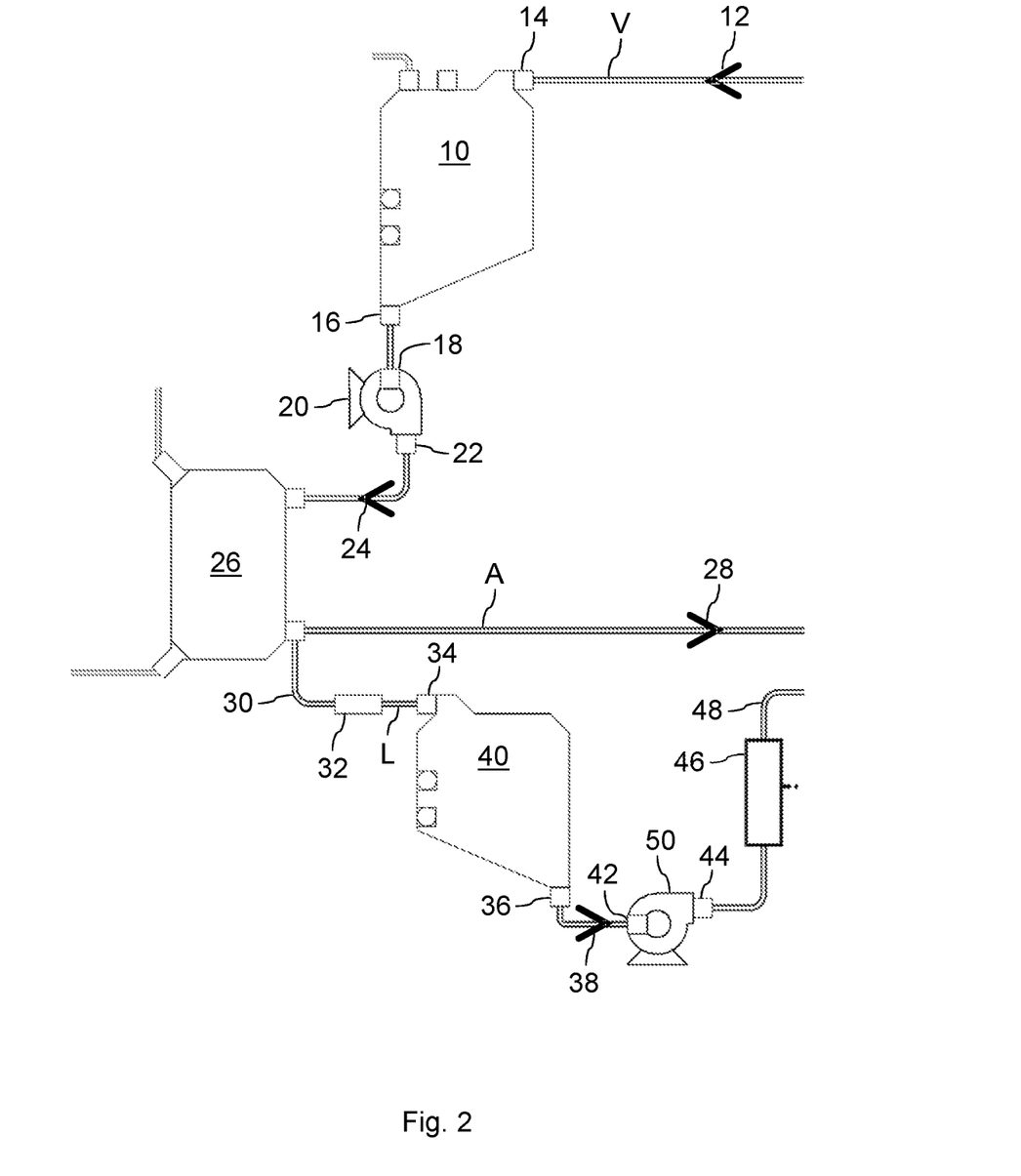
FIG. 2 shows a schematic arrangement of another exemplary embodiment of a cardioplegic agent delivery system.

FIG. 2 shows another embodiment of a cardioplegic agent delivery system. Where appropriate, similar components of the FIG. 2 system are provided with the same reference numerals as the FIG. 1 system. FIG. 2 shows components of a perfusion system, a venous line 12 supplying a blood reservoir 10 from where a pump 20 may transport blood towards an oxygenator 26 for the blood to be oxygenated and to be delivered, as arterial blood A, towards a patient in direction 28.

In the FIG. 2 system, the secondary flow path for the administration of cardioplegic solution is diverted from the arterial line A. The secondary flow path may be diverted directly from the oxygenator or at a location further downstream of the oxygenator. In any event, arterial blood entering the secondary flow path at a location 30 is in a highly pressurised condition and as such unsuitable for supplying a non-occlusive pump in a cardioplegia line. An intermediate reservoir 40 is provided in the secondary flow, comprising an intermediate reservoir inlet 34 and an intermediate reservoir outlet 36. To prevent highly pressurised blood from entering the intermediate reservoir 40, a clamp 32 is provided upstream of the intermediate reservoir 40 in the secondary flow path. The clamp 32 constitutes a pressure-isolating device, and so the pressure at a location L downstream of the clamp 32, before entering the intermediate reservoir inlet 34, is lower than at a location 30 upstream of the clamp 32.

The intermediate reservoir 40 may be provided in the form of a collapsible bag, akin to conventional venous reservoir bags. The intermediate reservoir 40 does not need to be capable of holding a large volume of blood, because the blood in the secondary flow path is merely required as a carrier fluid for the cardioplegic agent. As such, the capacity to hold blood of the intermediate reservoir 40 is smaller than the capacity to hold blood of the blood reservoir 10. The capacity of the intermediate reservoir 40 may be no more than ¾, ½, ¼, ⅕, or ⅒ of the capacity of the blood reservoir 10.

From the intermediate reservoir outlet 36, arterial blood, having a pressure below a minimum driving pressure, may be drawn in a direction indicated by arrow 38 by a centrifugal pump 50, through the pump inlet 42 through to the pump outlet 44. Downstream of the centrifugal pump 50, a cardioplegic agent delivery module 46 is provided, configured for administering cardioplegic agent into the carrier fluid stream. At a location 48 in the secondary flow path, downstream of the centrifugal pump 50 and the cardioplegic agent delivery module 46, the blood is in a condition for subsequent administration to a patient, i.e., the blood has the appropriate flow rate and driving pressure, and has the appropriate concentration of cardioplegic agent.

Figure 3:
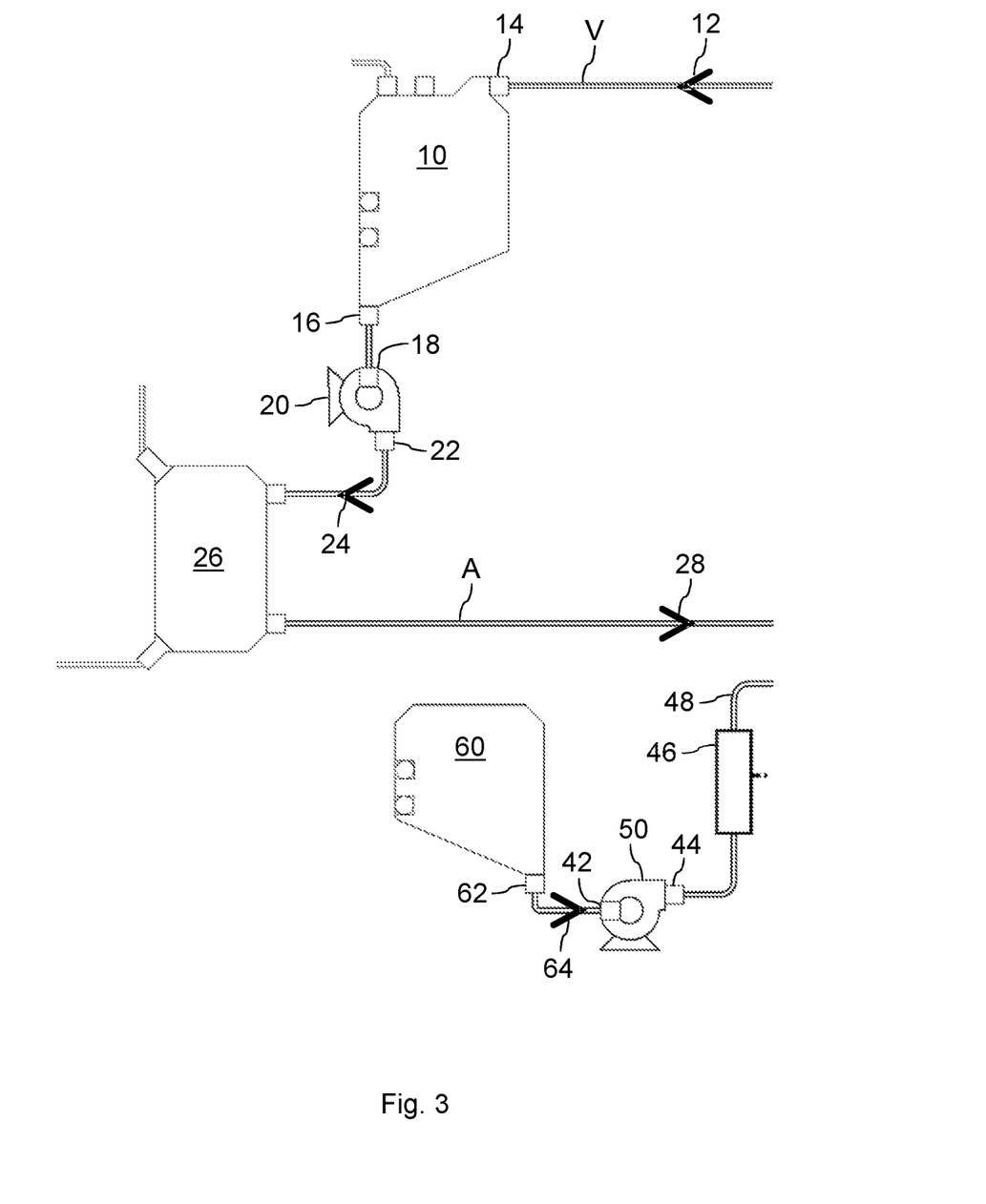
FIG. 3 shows a schematic arrangement of another exemplary embodiment of a cardioplegic agent delivery system.

FIG. 3 shows another embodiment of a cardioplegic agent delivery system. Similar components of the FIG. 3 system are provided with the same reference numerals as the FIG. 1 system and the FIG. 2 system. FIG. 3 also shows components of a perfusion system, a venous line 12 supplying a blood reservoir 10 from where a pump 20 may transport blood towards an oxygenator 26 for the blood to be oxygenated and to be delivered, as arterial blood A, towards a patient in direction 28.

In the FIG. 3 system, the cardioplegic agent delivery module is not using blood from a perfusion system as carrier fluid for the delivery of cardioplegic agent. The cardioplegic agent delivery system comprises a carrier fluid reservoir 60 with a carrier fluid reservoir outlet 62. The carrier fluid reservoir 60 may be provided in the form of a collapsible bag, akin to conventional venous reservoir bags. A carrier fluid, e.g., saline solution, is contained in the carrier fluid reservoir 60. The carrier fluid reservoir 60 does not need to be capable of holding a large volume of carrier fluid, because this is intended as a carrier fluid for the cardioplegic agent. As such, the capacity to hold carrier fluid of the carrier fluid reservoir 60 is smaller than the capacity of the blood reservoir 10. The capacity of the carrier fluid reservoir 60 may be no more than ¾, ½, ¼, ⅕, or ⅒ of the capacity of the blood reservoir 10.

The carrier fluid reservoir 60, constituting a supply reservoir, is configured to hold carrier fluid at or below atmospheric pressure, for instance by virtue of being positioned not higher than, or lower than the patient. As a consequence, the pressure of the carrier fluid in the carrier fluid reservoir 60 is below a minimum driving pressure.

From the carrier fluid reservoir outlet 62, the carrier fluid may be drawn in a direction indicated by arrow 64 by a centrifugal pump 50, through the pump inlet 42 and to the pump outlet 44. Downstream of the centrifugal pump 50, a cardioplegic agent delivery module 46 is provided, configured for administering cardioplegic agent into the carrier fluid. At a location 48 in the cardioplegic agent delivery system, downstream of the centrifugal pump 50 and the cardioplegic agent delivery module 46, the carrier fluid is in a condition for subsequent administration to a patient, i.e., the carrier fluid has the appropriate flow rate, and driving pressure, and has the appropriate concentration of cardioplegic agent.

In each of the systems shown in FIG. 1, 2, or 3, a back-flow prevention device may be installed downstream of the centrifugal pump, e.g., at a location 48. The back-flow prevention device may be actuated to prevent back flow into the cardioplegic agent delivery system due to a low pressure.

Atmospheric pressure is typically assumed to be in the region of 1 atm (corresponding to 101.325 kPa, or 760 mmHg), and the minimum driving pressure may be around 20 mmHg above atmospheric pressure. In embodiments, the minimum driving pressure may be around 10, 15, 20, 25, 30, 35, or 40 mmHg above atmospheric pressure.

The provision of a centrifugal pump provides a higher degree of accuracy for rendering the carrier fluid in a suitable condition (pressure and flow rate) so that it may subsequently be administered to a patient.

The invention claimed is:

1. A cardioplegic agent delivery system for use in a perfusion system, wherein the perfusion system includes a first pump for pumping blood towards an oxygenator, the blood being oxygenated by the oxygenator for delivery to a patient, the cardioplegic agent delivery system comprising:
   a supply reservoir for a carrier fluid for the cardioplegic agent,
   a delivery channel for the carrier fluid, the delivery channel leading from the supply reservoir to an outlet of the delivery channel,
   a second pump configured to effect a flow of the carrier fluid in the delivery channel from the supply reservoir to the outlet above a minimum driving pressure for the delivery of cardioplegic agent, wherein
   the supply reservoir is configured to hold carrier fluid below the minimum driving pressure, and
   the second pump is a centrifugal pump configured to receive carrier fluid from the supply reservoir and to effect a flow of the carrier fluid to the outlet at a flow rate and above the minimum driving pressure for the delivery of cardioplegic agent.

2. The cardioplegic agent delivery system according to claim 1, further comprising a back-flow prevention device downstream of the supply reservoir, to prevent flow from the delivery channel downstream of the supply reservoir into the supply reservoir.

3. The cardioplegic agent delivery system according to claim 1, further comprising a back-flow prevention device downstream of the centrifugal pump, to prevent flow from the delivery channel downstream of the centrifugal pump into the centrifugal pump.

4. The cardioplegic agent delivery system according to claim 2, wherein the back-flow prevention device comprises at least one selected from the group consisting of a back-flow prevention valve and an automated clamping system.

5. The cardioplegic agent delivery system according to claim 1, wherein the supply reservoir is a venous reservoir of the perfusion system.

6. The cardioplegic agent delivery system according to claim 1, wherein the supply reservoir is provided downstream of an oxygenator of the perfusion system, and wherein the delivery system further comprises a pressure-isolating device between the oxygenator and the supply reservoir, to provide that the pressure of the carrier fluid in the supply reservoir is below the minimum driving pressure independently of the pressure of the carrier fluid upstream of the pressure-isolating device.

7. The cardioplegic agent delivery system according to claim 6, wherein the system is further configured to receive an input indicative of the amount of carrier fluid in the supply reservoir, to make a determination as to whether or not the amount of carrier fluid is below a threshold level, and to actuate the pressure-isolating device to permit flow of carrier fluid into the supply reservoir.

8. The cardioplegic agent delivery system according to claim 1, wherein the outlet of the delivery channel supplies a cardioplegic line.

9. The cardioplegic agent delivery system according to claim 1, further comprising a cardioplegic agent inlet downstream of the second pump.

10. The cardioplegic agent delivery system according to claim 1, further comprising a level sensor configured to monitor the amount of fluid in the supply reservoir.

11. The cardioplegic agent delivery system according to claim 1, wherein the supply reservoir is or comprises a collapsible container.

12. The cardioplegic agent delivery system according to claim 1, further comprising a flow sensor for sensing the flow of the carrier fluid downstream of the centrifugal pump.

13. The cardioplegic agent delivery system according to claim 1, further comprising a pressure sensor for sensing the pressure of the carrier fluid downstream of the centrifugal pump.

14. The cardioplegic agent delivery system according to claim 1, further comprising a controller for controlling the centrifugal pump, in response to a control signal.

15. The cardioplegic agent delivery system according to claim 14, wherein the controller comprises a processor and software instructions implemented by the processor.

16. The cardioplegic agent delivery system according to claim 3, wherein the back-flow prevention device comprises at least one selected from the group consisting of a back-flow prevention valve and an automated clamping system.

17. The cardioplegic agent delivery system according to claim 2, further comprising a controller for controlling at least one selected from the group consisting of the centrifugal pump and the back-flow prevention device in response to a control signal.

18. The cardioplegic agent delivery system according to claim 3, further comprising a controller for controlling at least one selected from the group consisting of the centrifugal pump and the back-flow prevention device in response to a control signal.

19. The cardioplegic agent delivery system according to claim 6, further comprising a controller for controlling at least one selected from the group consisting of the centrifugal pump and the pressure-isolating device in response to a control signal.

* * * * *